United States Patent
Takai et al.

(10) Patent No.: US 7,309,810 B2
(45) Date of Patent: Dec. 18, 2007

(54) NONHUMAN MODEL ANIMAL SUFFERING FROM GUILLAIN-BARRÉ SYNDROME AND/OR FISHER SYNDROME

(75) Inventors: Toshiyuki Takai, Sendai (JP); Akira Nakamura, Sendai (JP); Akiko Sugahara, Sendai (JP); Kaori Yajima, Sendai (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/533,700

(22) PCT Filed: Oct. 29, 2003

(86) PCT No.: PCT/JP03/13958

§ 371 (c)(1),
(2), (4) Date: Oct. 28, 2005

(87) PCT Pub. No.: WO2004/039149

PCT Pub. Date: May 13, 2004

(65) Prior Publication Data

US 2007/0016966 A1    Jan. 18, 2007

(30) Foreign Application Priority Data

Oct. 29, 2002  (JP) .............................. 2002-315091

(51) Int. Cl.
*G01N 33/00* (2006.01)
*A01K 67/033* (2006.01)
*A01K 67/027* (2006.01)
*A01K 67/00* (2006.01)

(52) U.S. Cl. ................. 800/3; 800/18; 800/9

(58) Field of Classification Search ............ 800/3, 800/9, 18

See application file for complete search history.

(56) References Cited

OTHER PUBLICATIONS

Holschneider et al. Int J Devl Neuroscience, 2000, 18:615-618.*
Griffiths Microscopy Research and Technique 1998, 41: 344-358.*
Reinhard et al Adv Exp Med Biol. 1996; 398:241-6 (abstract only).*
Kennel et al Neurobiol Dis. Apr. 1996;3(2):137-47).*
Odaka et al J Neurol Neurosurg Psychiatry. 2001; 70(1):50-5.*
Yuki et al Ann Neurol, 2001, 49, 712-720.*
Chaudhry et al Seminar Opthalmol Oct.-Dec. 2006;21(4):223-7.*
Odaka et al J Neurol Neurosurg Psychiatry. Jan. 2001;70(1):50-5.*
Yuasa T. et al., Deletion of fc gamma receptor IIB renders H-2(b) mice susceptible to collagen-induced arthritis, J. Exp. Med. (1999), vol. 189, No. 1, p. 187-94.
Takai T. et al., Augmented humoral and anaphylactic responses in Fc gamma RII-deficient mice, Nature (1996), vol. 379, No. 6563, p. 346-49.
Odaka M. et al., N-glycolylneuraminic acid-containing GM1 is a new molecule for serum antibody in Guillain-Barre syndrome, Ann. Neurol. (1998), vol. 43, No. 6, p. 829-34.

\* cited by examiner

*Primary Examiner*—Anne-Marie Falk
*Assistant Examiner*—Anoop K Singh
(74) *Attorney, Agent, or Firm*—Morgan & Finnegan, L.L.P.

(57) ABSTRACT

The present invention intends to provide a non-human animal model of Guillain-Barré syndrome, which can be obtained by immunizing FcγRIIB-gene-deficient non-human animal with ganglioside GQ1$b$, and a screening method of a therapeutic agent for Guillain-Barré syndrome using the non-human animal model. A mouse model of Guillain-Barré syndrome is generated by immunizing FcγRIIB-gene-deficient mice with gangliosides GM1, GM2, GD1$a$, and GQ1$b$ together with Freund's adjuvant every three weeks four times in total.

2 Claims, 3 Drawing Sheets

RIIB-/-

WT

NONHUMAN MODEL ANIMAL SUFFERING FROM GUILLAIN-BARRÉ SYNDROME AND/OR FISHER SYNDROME

This application is a national phase entry of PCT application Ser. No. JP2003/013958, filed Oct. 29, 2003, which claims priority to and benefit of Japanese application No. 2002-315091, filed on Oct. 29, 2002, each of which is incorporated herein by reference in their entireties.

TECHNICAL FIELD

The present invention relates to a non-human animal model that develops Guillain-Barré syndrome (Fisher syndrome), more specifically to a non-human animal model of Guillain-Barré syndrome which can be obtained by immunizing with ganglioside GQ1b a non-human animal model whose FcγRIIB-gene is deficient in its chromosome (FcγRIIB-gene-deficient non-human animal model), and a screening method of a therapeutic agent for Guillain-Barré syndrome using the non-human animal model.

BACKGROUND ART

Guillain-Barré syndrome (GBS) is an inflammatory demyelinating disorder of peripheral nerves which occurs a few weeks after a flu-like symptom, and is characterized by rapidly-progressing flaccid-motor paralysis (weakness in muscles of all four limbs), loss of deep tendon reflexes, dysphagia, articulatory disorder, deep sensory disturbance, and vegetative neurosis (cardiac arrhythmia, blood pressure fluctuation). The frequency of Guillain-Barré syndrome is two cases in every 100,000 people per year, and 2,000 to 2,500 people are estimated to be newly affected by the disorder each year across Japan. However, not only is a therapeutic agent capable of achieving complete cure of the disorder undeveloped but also the cause and onset mechanism are yet to be clearly known, which entails the disorder's falling under so-called intractable diseases and being designated a special disease. Recently, plasma-exchange (plasmapheresis) and high-dose intravenous γ-globulin therapy have been reported to be effective treatments for the present syndrome. Further, with respect to the cause of the present syndrome, since autoantibody (anti-lipopolysaccharide antibody) against gangliosides appearing in peripheral nerves, which is associated with acuteness of the symptoms, has been detected in the patients' sera, gangliosides and autoimmune reaction have been pointed out to be closely linking to the onset mechanism. Gangliosides are classified into subclasses according to their molecular structures: GM1, GM2, GD1a, GD1b, GT1a, GQ1b and the like, and respective autoantibodies for each ganglioside are detected in sera of the patients with the disorder. In the aforementioned Guillain-Barré syndrome, it is particularly known that anti-GM1 antibody and anti-GD1a antibody appear as anti-ganglioside antibodies in the serum. Further, an elevated level of anti-GQ1b antibody is almost invariably and specifically observed in the sera in acute phase cases of Guillain-Barré syndrome with ocular muscle paralysis, and in Fisher syndrome cases.

Recently, Campylobacter jejuni, one of the bacteria responsible for foodpoisoning, has been pointed out to be relating to a cause of Guillain-Barré syndrome since there is a molecular homology between the lipopolysaccharide structure of Campylobacter and gangliosides, which may entail the appearance of auto-reactive T cells and B cells. However, it remains unproven whether the appearance of auto-reactive T cells and B cells including autoantibodies leads to any actual organic pathologies. In the animal-experiment level, although a case has been reported where rabbits were immunized with GD1b to develop peripheral neuropathy, there has been no such case where immunizing mice with various types of gangliosides led to their developing any pathological symptoms, which resulted in the absence of such disorder-mouse model suitable for Guillain-Barré syndrome. In cases like the above where rabbits and rats were induced to develop the disorder, the animals exhibited low incidence and mild symptoms which made themselves inappropriate for the model. Further, the absence of suitable model has prevented the development of a therapeutic agent and method.

Likewise, Fisher syndrome is known as a variant of Guillain-Barré syndrome. About 5% of Guillain-Barré syndrome cases are estimated to fall under the aforementioned Fisher syndrome, whose symptoms include external ophthalmoplegia, diplopia, ataxia, loss of tendon reflexes, and facial nerve palsy, with a preceding infection of the upper respiratory tract and the like. The symptoms are identical to those of Guillain-Barré syndrome except that quadriplegia is not induced in humans. Further, in Fisher syndrome cases, elevated level of blood-IgG-antibody titer against ganglioside GQ1b has been reported while as with the case of the above Guillain-Barré syndrome, onset mechanism is unknown and the therapeutic agent is yet to be developed.

The acuteness of these disorders is at its peak about a month after the first symptom appears, gradually getting milder with the recovery period of a few months to a year. The prognosis for the patients with these disorders is relatively good, but the cases with residual deficits are not rare. Moreover, since the patients are forced to experience mental distress, hospitalization and outpatient visits over about a year, the development of the therapeutic agent and treating method for the disorder is ardently awaited by the medical-service community including patients, their families, and physicians.

Meanwhile, on cell surfaces of the immune system and the like, receptors which recognize and bind to Fc part of Ig (hereinafter referred to as "FcR") are present, among which, Fcγ receptors, the receptor proteins which specifically bind to γ chain of IgG in body fluid (hereinafter referred to as FcγR), are broadly classified into three types based on the gene-structure similarity: Type I (CD64 antigen), Type II (CD32 antigen), and Type III (CD16 antigen). In contrast to other FcRs, FcγRII has low affinity for monomeric IgG and binds to multivalent IgG that has become an immunocomplex, to broadly appear on blood-forming stem cells including monocytes, macrophages, polymorphonuclear leukocytes (PMN), mast cells, blood platelets, some T-cell lymphocytes and some B-cell lymphocytes. Further, there present three types of receptors of FcγRII differing in gene sequences: FcγRIIA, FcγRIIB, and FcγRIIC. All these receptors are mapped to the chromosome 1q23 region.

Unlike other FcRs, the above FcγRIIB possesses an amino-acid sequence which transmits inhibitory signals to intracellular domains without associating with γ chain (ITIM: Immunoreceptor Tyrosine-based Inhibition Motif) (Immunol. Rev. 125, 49-76, 1992, Science 256, 1808-1812, 1992). To elucidate such physiological functions of FcγRIIB, the present inventors have already generated FcγRIIB-deficient mice (Nature 379, 346-349, 1996), as well as arthritis-mouse model which can be obtained by immunizing FcγRIIB-deficient mice with Type II collagen (J. Exp. Med. 189, 187-194, 1999), and autoimmune-disorder animal model (Japanese Laid-Open Patent Application No. Heisei 08-289699).

Previously, appropriate animal model for investigating the onset mechanism of Guillain-Barré syndrome, an inflammatory demyelinating disorder, did not exist. The object of the present invention is to provide non-human animal model that developes Guillain-Barré syndrome (Fisher syndrome) and more specifically, to provide non-human animal model of Guillain-Barré syndrome which can be obtained by immunizing FcγRIIB-gene-deficient non-human animal with ganglioside GQ1b, and a screening method of a therapeutic agent for Guillain-Barré syndrome using the aforementioned non-human animal model.

The present inventors made a keen study to solve the above problem and they endeavored to generate Guillain-Barré syndrome mouse model by using FcγRIIB-gene-deficient mice and immunized them with gangliosides GM1, GM2, GD1a and GQ1b together with Freund's adjuvant every three weeks four times in total. As a result, of those immunized with ganglioside antigen, FcγRIIB-gene-deficient mice immunized with GQ1b exhibited peripheral neuropathy in which paralysis of their tails and hind legs was observed. These mice demonstrated an elevated level of antibody titer against GQ1b, which symptom appeared consistent with that of Fisher syndrome, a variant of Guillain-Barré syndrome, where humans are commonly observed to develop autoantibody against GQ1b. The present inventors have thus completed the present invention by discovering that a new disorder-mouse model can be generated for Guillain-Barré syndrome (Fisher syndrome). The present inventors have also established a screening method of an effective therapeutic agent for the syndrome based on the present invention.

DISCLOSURE OF THE INVENTION

The present invention relates to: a mouse model of Guillain-Barré syndrome which can be obtained by immunizing with gangliosides GQ1b a mouse whose FcγRIIB-gene is deficient in its chromosome to develop Guillain-Barre syndrome ("1"); a mouse model of Guillain-Barré syndrome, wherein Guillain-Barré syndrome is Fisher syndrome ("2"); the mouse model of Guillain-Barré syndrome according to "1" or "2", which develops a peripheral neuropathy wherein paralysis of its tail and hind legs occurs ("3").

The present invention further relates to: a screening method of a therapeutic agent for Guillain-Barré syndrome wherein a test substance is administered to the mouse model of Guillain-Barré syndrome according to any one of "1" to "3", to observe and assess the degree of symptoms of Guillain-Barré syndrome in the mouse model of the syndrome ("6"); a screening method of a therapeutic agent for Guillain-Barré syndrome and/or Fisher syndrome wherein a test substance is administered to the mouse model of Guillain-Barré syndrome according to any one of "1" to "3", to measure and assess the level of anti-GQ1 antibody appearance ("7"); and a therapeutic agent that can be obtained by the screening method of a therapeutic agent for Guillain-Barré syndrome according to "6" or "7" ("8").

BEST MODE OF CARRYING OUT THE INVENTION

Figure 1:
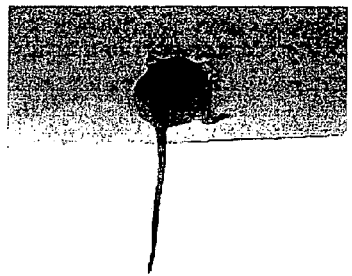
FIG. 1 is a set of photographs of the non-human animal model of Guillain-Barré syndrome and/or Fisher syndrome of the present invention with paralysis in its tail and hind legs (upper figure; RIIB$^{-/-}$), and a wild-type mouse (lower figure; WT) used as a control.
Figure 1:
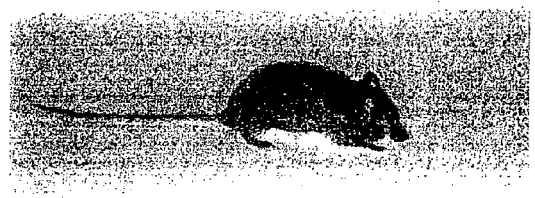
Figure 1:
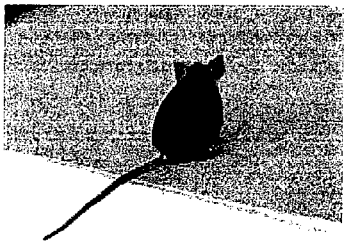
Figure 1:
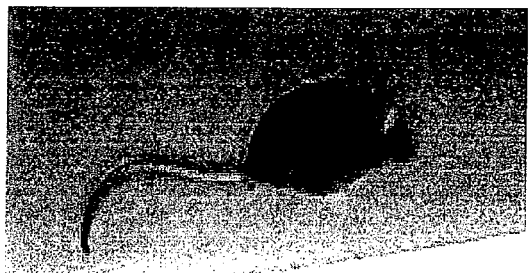

As for the non-human animal model of Guillain-Barré syndrome of the present invention, there is no particular limitation as long as it is obtained by immunizing with ganglioside GQ1b the non-human animal whose FcγRIIB-gene is deficient in its chromosome, and is a non-human animal that develops Guillain-Barré syndrome. Here Guillain-Barré syndrome indicates a non-hereditary disorder characterized by rapidly-progressing flaccid-motor paralysis (weakness in muscles of all four limbs), loss of deep tendon reflexes, dysphagia, articulatory disorder, deep sensory disturbance, and vegetative neurosis (cardiac arrhythmia, blood pressure fluctuation) which occurs a few weeks after a flu-like symptom, and other similar disorders. If the Guillain-Barré syndrome is developed, level of antibody titer against ganglioside GQ1b in the serum rises and more specifically, external ophthalmoplegia, diplopia, ataxia, loss of tendon reflexes, facial nerve palsy, peripheral neuropathy of tail and hind legs and the like are induced. Furthermore, Fisher syndrome is a variant of Guillain-Barré syndrome, whose symptoms are identical to those of Guillain-Barré syndrome except that quadriplegia is not induced in humans.

As for the FcγRIIB-gene-deficient non-human animal model of the present invention, any model animals are accepted as long as its FcγRIIB-gene is deficient in its chromosome, although it can be preferably exemplified by rodents such as mice and rats, in particular, by the mouse whose FcγRIIB-gene is deficient in its chromosome. The mouse whose FcγRIIB-gene is deficient in its chromosome can be generated according to the method previously described by the present inventors (Nature 379, 346-349, 1996) and the like. In concrete terms, FcγRIIB-knockout mouse can be obtained according to the following process: FcγRIIB gene is screened using a gene fragment derived from the mouse gene library by a method such as PCR and the like; the screened FcγRIIB gene is subcloned using a viral vector and the like, then determined by DNA sequencing; a target vector is prepared by substituting the fragment containing $S_2$ exon and $EC_1$ exon of the clone to a pMC1 neo gene cassette and the like; the linearized vector is introduced into ES cells by electroporation and the like to cause homologous recombination; from among the homologous recombinants, ES cells showing resistance to G418 and the like are selected, and the clones of those cells are microinjected into a murine blastocyst; the blastocyst is placed back to the host parent to generate a chimeric mouse; when this chimeric mouse is intercrossed with a wild-type mouse, a heterozygous mouse can be obtained; by intercrossing the heterozygous mice, an FcγRIIB-knockout mouse can be obtained.

As for the generating method for a non-human animal model of Guillain-Barré syndrome of the present invention, any methods are accepted without particular limitation as long as it can provide a non-human animal model of Guillain-Barré syndrome, although it can be preferably exemplified by the method wherein ganglioside GQ1b is used as an antigen to immunize the above FcγRIIB-gene-deficient non-human animal. Further, as for the method for immunizing, no particular limitation is set although it can be preferably exemplified by the method wherein GQ1b antigen is used together with complete Freund's adjuvant in the first immunization, and afterwards together with incomplete Freund's adjuvant every three weeks. Additionally, it is desirable to repeat the immunization 3 to 6 times in total, of which 4 times is particularly preferable.

Ganglioside GQ1b used in the present invention is sphingoglycolipid comprising four sialic acids (Sia), with the structure of Galβ1→3 (3←2αSia3←2αSia) GalNAcβ1→4Galβ1→4(3←2αSia3←2αSia) Glcβ→1'Cer, produced from lactosylceramide (Cer) in the synthetic pathway b. Among these, the binding form of 3←2αSia, a peculiar sugar chain, characterizes the property of the GQ1b. Further, a specific antibody has been obtained for each ganglioside. Since antibodies recognizing respective gangliosides recognize the difference in the binding form of the above sugar chain, 3←2αSia, GQ1b (monoclonal) antibody also appears to be recognizing the four binding forms of 3←2αSia specifically.

As for the screening method of a therapeutic agent for Guillain-Barré syndrome of the present invention, there is no particular limitation as long as it can confirm and select the pharmacological effects of the therapeutic agent using the non-human animal model of Guillain-Barré syndrome of the present invention, although it can be specifically exemplified by the method wherein a test substance is administered orally or parenterally to the non-human animal model of Guillain-Barré syndrome of the present invention, to observe and assess the degree of symptoms in chronological order by scoring the level of the disorder (degree of alleviation), and also by the method wherein a test substance is administered to the non-human animal model of the Guillain-Barré syndrome of the present invention to measure and assess the appearance level of the anti-GQ1b antibody in the blood of the non-human animal model. As for a method for measuring the appearance level of the above anti-GQ1b antibody in the blood, it can be specifically exemplified by ELISA analysis using secondary antibody.

The therapeutic agent for Guillain-Barré syndrome obtained by the above screening method of the present invention can be used to treat patients developing Guillain-Barré syndrome (Fisher syndrome). The therapeutic agent for Guillain-Barré syndrome of the present invention can be administered orally or parenterally. An oral administration can be in the form of solid preparation such as powder, granule, capsules, and tablets, and also of liquid preparation such as syrup and elixir whereas pareteral administration can be in the form of injection, transcutaneous preparation, suppository and the like. These preparations can be produced according to the conventional procedure by adding auxiliaries, that are pharmacologically and galenical pharmaceutically acceptable, to active ingredients. Further, dosage can vary according to the type of disorder to be treated, age, sex, weight, symptom, and the form of administration, to suit each patient.

The present invention will be described in detail with reference to the following examples, while the technical scope of the present invention will not be limited to these examples.

REFERENCE EXAMPLE

Generation of FcγRIIB-Deficient Mice

A clone of genomic DNA of FcγRIIB gene was isolated by screening the genomic DNA library of 129/Sv/J (H-2b) mouse. A 2.65 Kb fragment containing two independent exons i.e. $S_2$ and $EC_1$ of the clone was substituted by a pMC1 neo gene cassette (Toyobo) to construct a target vector. The linearized vector was introduced into ES cells (J1) by electroporation to cause homologous recombination.

ES clones were isolated from the above ES cells wherein homologous recombination has occurred, then neomycin-resistant ES clones were screened for G418 and GANC (gancyclovir), and a homologous recombinant was identified by Southern Blot Analysis. Genomic DNA was isolated from the identified homologous recombinant and digested with HindIII. Then it was verified that targeted allele containing pMC1 neo gene cassette was included. The verified ES clones were microinjected into a blastocyst to generate a chimeric mouse. The generated chimeric mouse then was intercrossed with a wild-type C57BL/6(H-2b) mouse to generate a heterozygous mouse. Further, in order to obtain a homozygous mouse the heterozygous mice were intercrossed to generate a mouse whose FcγRIIB gene is deficient in its chromosome, and a wild-type mouse.

Example 1

Immunization of FcγRIIB-Gene-Deficient Mice

As gangliosides, GM1, GM2, GD1a, GD1b and GQ1b (all ALEXIS) were used. Two types of emulsions were prepared: one by mixing in coupled syringes 1 ml of each ganglioside solution of the concentration rate of 1 mg/ml, respectively with 3 mg/ml of complete Freund's adjuvant (CFA) consisting of liquid paraffin, surfactant, and killed mycobacterium tuberclosis; the other by mixing in coupled syringes 1 ml of each ganglioside solution of the concentration rate of 1 mg/ml, respectively with 3 mg/ml of incomplete Freund's adjuvant (IFA) consisting of liquid paraffin and surfactant.

The FcγRIIB-gene-deficient mice generated by the method according to the above Reference Example (8 weeks old: no difference between the sexes was observed in terms of the test results) (n=5), anesthetized by ether and shaven on the dorsocaudal side, were injected intracutaneously with 150 μl of emulsion consisting of 50 μg of respective ganglioside and 100 μg of CFA to be primarily immunized, then with 150 μl of emulsion consisting of 50 μg of respective ganglioside and 100 μg of IFA every three weeks three times in total, in endeavoring to generate the mice of Guillain-Barré syndrome. Additionally, wild-type mice (n=5) were used as a control. Consequently, the FcγRIIB-gene-deficient mice immunized with GQ1b exhibited peripheral neuropathy wherein paralysis of their tails and hind legs occurred. The mice demonstrated spread hind legs, inability of walking, and drooping tails (FIG. 1; RIIB$^{-/-}$). Meanwhile, the paralysis and the like were not observed in FcγRIIB-gene-deficient mice immunized with GM1, GM2, GD1a, and GD1b, as well as in the wild-type mice (FIG. 1; WT) used as a control.

Example 2

Paralytic Symptom Scores

Figure 2:
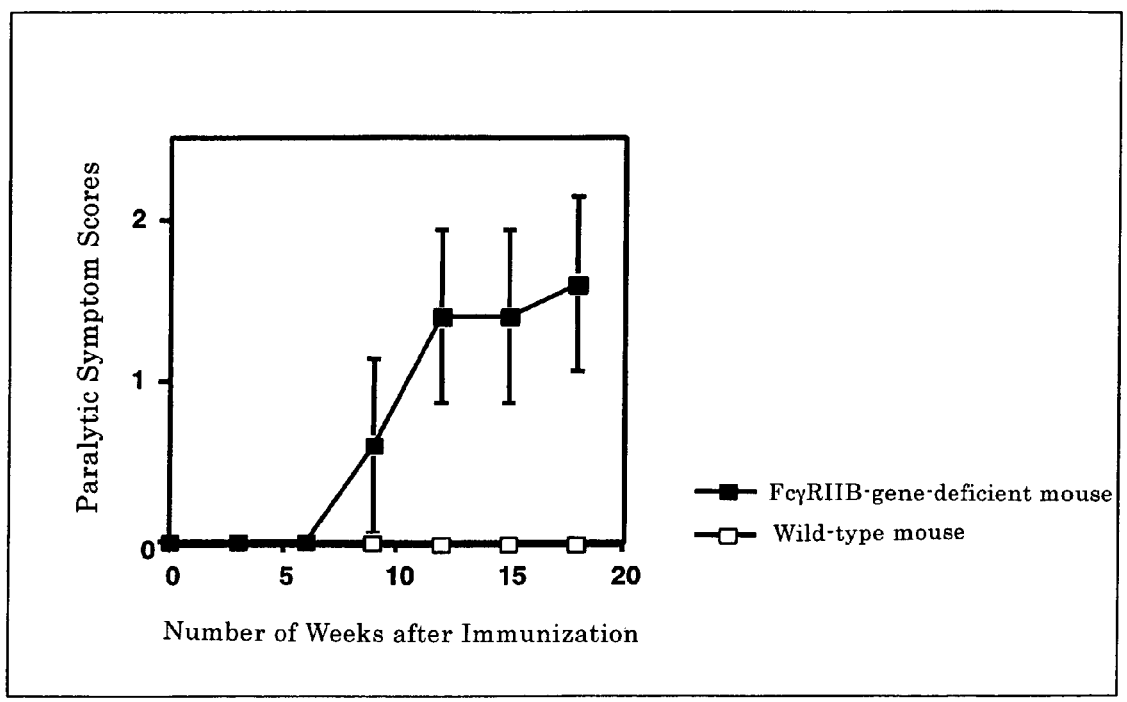
FIG. 2 shows paralytic symptom scores for the non-human animal model of Guillain-Barré syndrome and/or Fisher syndrome of the present invention, and for the wild-type mouse used as a control.

The wild-type mice and FcγRIIB-gene-deficient mice immunized with GQ1b, were scored for an assessment into five levels according to their symptoms: 0 point-no symptom; 1 point-paralysis of the tail; 2 points-paralysis of the tail and both hind legs; 3 points-paralysis of the tail and all four limbs; 4 points-death. The result is shown in FIG. 2. Meanwhile in FIG. 2, white squares (□) represent the scores for the wild-type mice and black squares (■) those for FcγRIIB-gene-deficient mice. As a result, FcγRIIB-gene-deficient mice immunized with GQ1b were observed to develop Guillain-Barré syndrome (Fisher syndrome) (FIG. 2).

Example 3

Level of Serum Antibody Titer Against GQ1b

Figure 3:
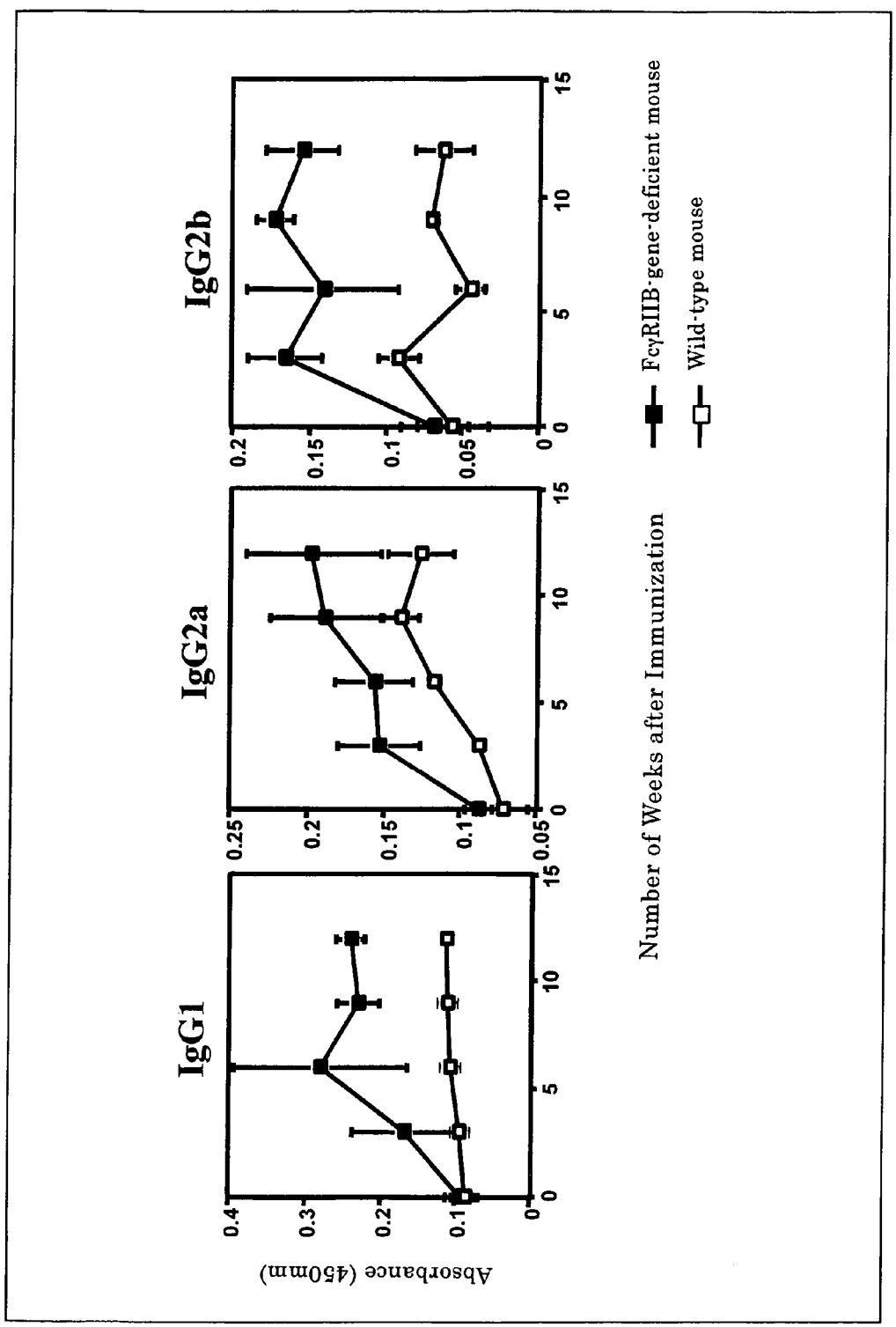
FIG. 3 shows antibody titer of anti-GQ1b antibody IgG1, IgG2a and IgG2b in the serum of the non-human animal model of Guillain-Barré syndrome and/or Fisher syndrome of the present invention, and of the wild-type mouse used as a control.

In addition, blood samples of wild-type mice and FcγRIIB-gene-deficient mice both immunized with GQ1b were collected from their orbits 3, 6, 9, and 12 weeks after the primary immunization to examine the level of antibody titer against GQ1b by employing the following improved ELISA analysis provided in a literature (Cell. Immunol. 145, 299-310, 1992). 5 μg of GQ1b was dissolved in 1 ml of 50 mM sodium bicarbonate solution (pH=8.5) to be used at the rate of 50 μl per well for coating positively-charged 96-well micro plates (NUNC) overnight at 4° C. Subsequently, the plates were washed once with PBS containing 0.05% of Tween 20 and 0.1% of BSA, and left overnight at 4° C. in 250 μl of PBS containing 0.5% of BSA per well for blocking. The sera derived from the above blood and diluted by 500 folds were then added to the above 96-well micro plates at the rate of 50 μl per well to be reacted overnight at 4° C. Following the reaction, the 96-well micro plates were washed three times with PBS containing 0.05% of Tween 20, added 50 μl of 500-fold-diluted goat-anti-mouse IgG1, IgG2a or IgG2b binding to peroxidase (Sigma), and incubated for two hours at 4° C., and after the incubation, were re-washed three times with PBS including 0.05% of Tween20, went through 30-minute enzymatic reaction with 50 μl of True Blue Peroxidase Substrate (Kirkegaard & Perry Labs) at ambient temperature. OD450 was then measured by a micro-plate reader (Biolumin 960; Molecular Dynamics). The result is shown in FIG. 3. Meanwhile in FIG. 3, white squares (□) represent the absorbance of the wild-type mice and black squares (■) that of FcγRIIB-gene-deficient mice. These results have shown that FcγRIIB-knockout mice (IIB-KO) displayed more increased level of antibody titer (IgG1, IgG2a, and IgG2b) against GQ1b than the wild-type mice (Wild), which is consistent with the observation of Guillain-Barré syndrome (Fisher syndrome). It was thus found that a model mouse of Guillain-Barré syndrome (Fisher syndrome) can be generated.

INDUSTRIAL APPLICABILITY

Since the non-human animal model of Guillain-Barré syndrome and/or Fisher syndrome of the present invention exhibited paralysis of its tail and hind legs and displayed an elevated level of antibody titer against gangliosides, they are deemed to have developed symptoms consistent with Guillain-Barré syndrome and Fisher syndrome, a variant of the aforementioned syndrome, in humans and can be utilized for developing the therapeutic method and agent for treating these symptoms.

The invention claimed is:

1. A mouse model of Guillain-Barré syndrome obtained by immunizing a homozygous FcγRIIB gene deficient mouse with GQ1b ganglioside, wherein said mouse model develops peripheral neuropathy leading to paralysis of its tail and hind legs and elevated levels of antibody titer against GQ1b occurs.

2. A screening method of identifying a candidate agent for treatment of Guillain-Barré syndrome comprising,
   (i) administering a test substance to the mouse model of claim 1;
   (ii) measuring the level of anti-GQ1b antibody present in said mouse model of the syndrome; and
   (iii) observing said mouse model of the syndrome for the degree of peripheral neuropathy wherein paralysis of the tail and hind legs occurs;
   wherein said test substance has an effect against Guillain-Barré syndrome when the level of anti-GQ1b antibody and the degree of peripheral neuropathy are decreased, as compared to said mouse model not receiving the test substance.

* * * * *